US00PP28512P2

(12) United States Plant Patent
Koekkoek

(10) Patent No.: US PP28,512 P2
(45) Date of Patent: Oct. 10, 2017

(54) CARNATION PLANT NAMED 'HILKAYLEE'

(50) Latin Name: ***Dianthus* L.**
Varietal Denomination: Hilkaylee

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 14/999,648

(22) Filed: Jun. 8, 2016

(51) Int. Cl.
*A01H 5/02* (2006.01)

(52) U.S. Cl.
USPC ..... Plt./272

(58) Field of Classification Search
USPC ..... Plt./272
See application file for complete search history.

*Primary Examiner* — Annette Para
(74) *Attorney, Agent, or Firm* — C. A. Whealy

(57) ABSTRACT

A new and distinct cultivar of Carnation plant named 'Hilkaylee', characterized by its compact, uniformly mounding and upright to broadly spreading plant habit; relatively small leaves; freely flowering habit; light pink and red purple bi-colored semi-double flowers; and good container performance.

1 Drawing Sheet

Botanical designation: *Dianthus* L.
Cultivar denomination: 'HILKAYLEE'.

BACKGROUND OF THE INVENTION

The present invention relates to a new and distinct cultivar of Carnation plant, botanically known as *Dianthus* L., grown commercially as a container plant and hereinafter referred to by the name 'Hilkaylee'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in June, 2011 of *Dianthus* L. 'Charmy', not patented, as the female, or seed, parent with *Dianthus caryophyllus* 'Bianca', disclosed in U.S. Plant Pat. No. 7,112, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal cuttings propagated in a controlled greenhouse environment in De Kwakel, The Netherlands since October, 2012 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilkaylee'. These characteristics in combination distinguish 'Hilkaylee' as a new and distinct Carnation plant:

1. Compact, uniformly mounding and upright to broadly spreading plant habit.
2. Relatively small leaves.
3. Freely flowering habit.
4. Light pink and red purple bi-colored semi-double flowers.
5. Good container performance.

Plants of the new Carnation differ primarily from plants of the female parent, 'Charmy', in the following characteristics:

1. Plants of the new Carnation have slightly larger flowers than plants of 'Charmy'.
2. Flowers of plants of the new Carnation have more petals than flowers of plants of 'Charmy'.
3. Plants of the new Carnation and 'Charmy' differ in flower color as plants of 'Charmy' have white and red purple bi- colored flowers.

Plants of the new Carnation differ primarily from plants of the male parent, 'Bianca', in the following characteristics:

1. Plants of the new Carnation are more freely flowering than plants of 'Bianca'.
2. Plants of the new Carnation have smaller flowers than plants of 'Bianca'.
3. Flowers of plants of the new Carnation have fewer petals than flowers of plants of 'Bianca'.
4. Plants of the new Carnation and 'Bianca' differ in flower color as plants of 'Bianca' have white and red purple bi- colored flowers.

Plants of the new Carnation also can be compared to plants of *Dianthus caryophyllus* 'Margarita', disclosed in U.S. Plant Pat. No. 17,335. In side-by-side comparisons, plants of the new Carnation differ primarily from plants of 'Margarita' in the following characteristics:

1. Plants of the new Carnation are more freely branching than plants of 'Margarita'.

2. Plants of the new Carnation have shorter branches than plants of 'Margarita'.
3. Plants of the new Carnation and 'Margarita' differ in flower color as plants of 'Margarita' have white and red purple-colored flowers.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilkaylee' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 17° C., night temperatures averaged 12° C. and light levels averaged 7,000 lux. Plants used for the photograph and description were twelve weeks old. In the following description, color references are made to The Royal Horticultural Society Colour Chart, 2015 Edition, except where general terms of ordinary dictionary significance are used.

Botanical classification: *Dianthus* L. 'Hilkaylee'.

Parentage:

*Female, or seed, parent.*—*Dianthus* L. 'Charmy', not patented.

*Male, or pollen, parent.*—*Dianthus caryophyllus* 'Bianca', disclosed in U.S. Plant Pat. No. 7,112.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; growth habit, moderate to low vigor.

*Plant height, soil level to top of foliar plane*.—About 11.5 cm.

*Plant height, soil level to top of floral plane*.—About 12.5 cm.

*Plant diameter or spread*.—About 20.9 cm.

*Lateral branches*.—Branching habit: Freely branching habit with about seven main (basal) stems; each main stem with about six lateral branches; pinching enhances lateral branch development. Length; About 8.4 cm. Diameter: About 2.5 mm to 3 mm. Internode length: About 2.6 cm. Strength: Strong. Aspect: Upright to about 70° from vertical. Texture and luster: Smooth, glabrous, waxy cuticle; matte. Color, developing: Close to 142B; at internodes, close to 144C. Color, developed: Close to 137B; thin waxy cuticle, close to 188B.

Leaf description:

*Arrangement*.—Opposite, simple; sessile.

*Length*.—About 7.8 cm.

*Width*.—About 6 mm.

*Shape*.—Narrowly oblanceolate; moderately carinate.

*Apex*.—Acute.

*Base*.—Attenuate; decurrent.

*Margin*.—Entire.

*Texture and luster, upper and lower surfaces*.—Smooth, glabrous; matte.

*Venation pattern*.—Parallel.

*Color*.—Developing leaves, upper and lower surfaces: Close to 143B; towards the base, close to 144B. Fully expanded leaves, upper surface: Close to NN137A; venation, close to NN137A. Fully expanded leaves, lower surface: Close to NN137C; venation, close to 144A.

Flower description:

*Flower form and flowering habit*.—Semi-double flowers arranged singly, in pairs or in clusters of three to four flowers; freely flowering habit with about 150 flowers developing during the flowering season; flowers face mostly upright to slightly outwardly.

*Natural flowering season*.—Flowering is continuous from the spring to late summer in The Netherlands; plants begin flowering about nine to eleven weeks after planting.

*Postproduction longevity*.—Flowers last about ten days on the plant; flowers not persistent.

*Fragrance*.—Moderately fragrant; clove-like, sweet.

*Flower buds*.—Length: About 2.9 cm. Diameter: About 8 mm. Shape: Oblong. Texture and luster: Smooth, glabrous; matte. Color: Close to 137B; towards the base, close to 144B; petal apices, close to 157B.

*Cluster height*.—About 3.5 cm.

*Cluster diameter*.—About 5.6 cm.

*Flower diameter*.—About 4.2 cm.

*Flower depth*.—About 3.5 cm.

*Petals*.—Quantity and arrangement: About ten petals arranged in two whorls. Length: About 3.9 cm. Width: About 2.2 cm. Shape: Spatulate. Apex: Praemorse; slightly crinkled. Base: Narrowly cuneate. Margin: Towards the apex, irregularly dentate; towards the base, entire; slightly undulate. Texture and luster, upper and lower surfaces: Smooth, glabrous; slightly velvety; matte. Color: When opening, upper surface: Towards the margins and apex, close to 69D; center, close to 187A with two or three irregularly-shaped blotches, close to 68B; towards the base, close to 75B to 75C; at the base, close to 145C. When opening, lower surface: Lighter than between N170D and 186D; proximal half, strongly tinged with close to 185D; at the base, close to 145C. Fully opened, upper surface: Towards the margins and apex, close to 69D; center, close to 187C with two or three irregularly-shaped blotches, close to 68B and 75C; towards the base, close to 75B; at the base, close to 145C; with development, distally, close to NN155D and proximally, between 59A and 187C with irregular stripes and blotches, close to 64C; towards the base, close to 75B and at the base, close to 145C; venation, similar to lamina colors. Fully opened, lower surface: Close to between 65B and 75C; proximal half, tinged with close to 64B; at the base, close to 145C; with development, color becoming closer to NN155B slightly tinged with close to 75C to 75D and at the base, close to 145C; venation, similar to lamina colors. Petaloids: Petaloid development has not been observed on plants of the new Carnation.

*Sepals*.—Quantity and arrangement: Five sepals arranged in a single whorl; proximal 70% portion of the sepals are fused into a campanulate-shaped calyx. Calyx length: About 2.2 cm. Calyx diameter: About 9 mm. Sepal length: About 2.2 cm. Sepal width, at base of "free" portion: About 5 mm. Shape: Narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 147D. When opening, lower surface: Close to 137B; towards the base, close to 144B. Fully opened, upper surface: Close to 147D. Fully opened, lower surface: Close to NN137A; towards the base, close to 144B.

*Peduncles*.—Length: About 1 mm. Diameter: About 1 mm. Strength: Moderately strong. Aspect: About 40° from the stem axis. Texture and luster: Smooth, glabrous; moderately glossy. Color: Close to 144A.

*Reproductive organs*.—Stamens: Quantity: About ten stamens per flower; strongly deformed. Filament length: About 2.2 cm. Filament color: Close to NN155D. Anther length: About 3 mm. Anther shape: Oblong. Anther color: Close to 186C. Pollen; Moderate. Pollen color: Close to 158C to 158D. Pistils: Quantity: About two per flower. Pistil length: About 1.6 cm. Stigma diameter: About 3 mm. Stigma shape: Pointed, spirally curved. Stigma color: Close to NN155D. Style length: About 1.3 cm. Style color: Close to NN155D. Ovary color: Close to 145A; towards the base, close to 157C. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be suitable for USDA Hardiness Zones 5 to 9.

It is claimed:

1. A new and distinct Carnation plant named 'Hilkaylee' as illustrated and described.

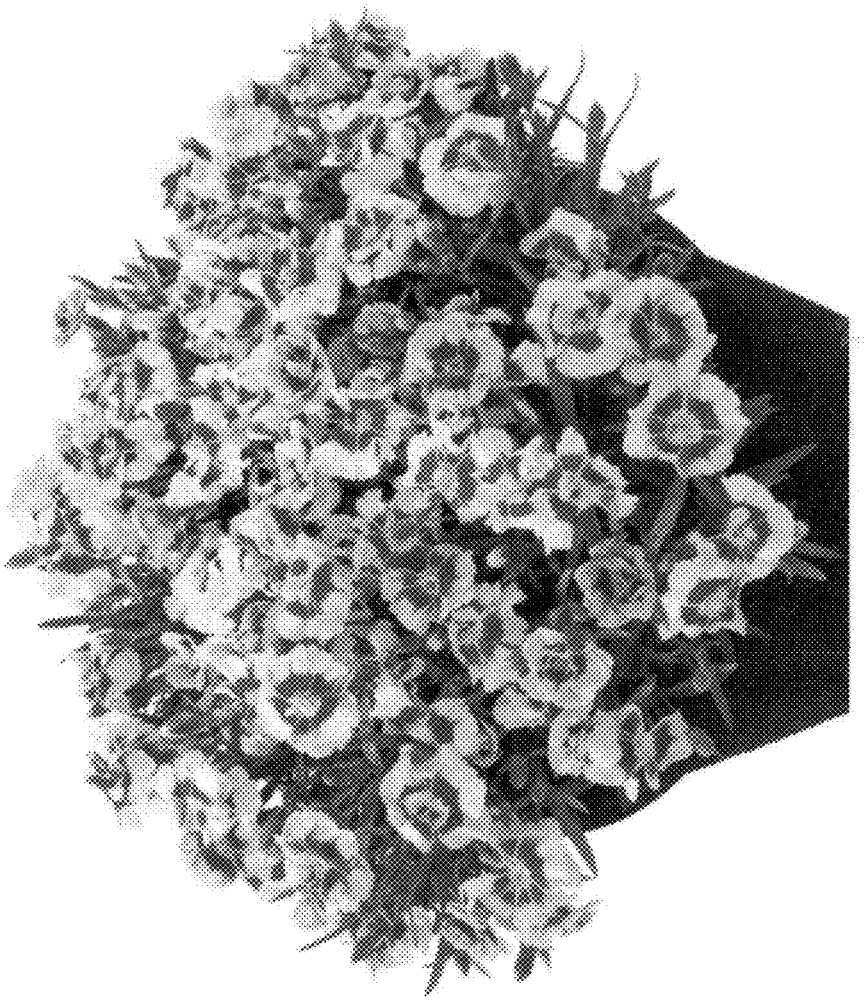

* * * * *